United States Patent [19]

Viswanathan et al.

[11] Patent Number: 4,917,685
[45] Date of Patent: Apr. 17, 1990

[54] DELIVERY DEVICE FOR THE ADMINISTRATION OF STABILIZED GROWTH PROMOTING HORMONES

[75] Inventors: Ravi Viswanathan; Randolph B. DePrince, both of Terre Haute, Ind.

[73] Assignee: International Minerals & Chem. Corp.

[21] Appl. No.: 863,885

[22] Filed: May 16, 1986

[51] Int. Cl.⁴ .............................................. A61K 9/22
[52] U.S. Cl. .................................. 604/891.1; 530/399
[58] Field of Search ................... 604/890.92; 530/399; 514/2, 21

[56] References Cited

U.S. PATENT DOCUMENTS

| | | |
|---|---|---|
| 3,056,724 | 10/1962 | Blackshear et al. . |
| 3,279,996 | 10/1966 | Long et al. . |
| 4,013,762 | 3/1977 | Bensen et al. ..................... 514/178 |
| 4,096,239 | 6/1978 | Katz et al. ......................... 604/891 |
| 4,164,560 | 8/1979 | Folkman et al. .................. 604/891 |
| 4,179,337 | 12/1979 | Davis et al. . |
| 4,180,560 | 12/1979 | Katz et al. ......................... 604/891 |
| 4,191,741 | 3/1980 | Hvelsen et al. .................... 604/891 |
| 4,259,320 | 3/1981 | De Lay ............................... 424/118 |
| 4,439,181 | 3/1984 | Marston . |
| 4,450,150 | 5/1984 | Sidman .............................. 604/891 |
| 4,521,709 | 6/1985 | Bawman ............................ 514/2 |
| 4,562,197 | 12/1985 | Snavey et al. ..................... 514/343 |

FOREIGN PATENT DOCUMENTS 3228533  2/1984  Fed. Rep. of Germany ...... 604/891

Primary Examiner—C. Fred Rosenbaum
Assistant Examiner—Mark F. Colosimo

[57] ABSTRACT

The present invention relates to a delivery device designed to be implanted in an animal and for the administration of a stabilized growth promoting formulation. This device has a wall formed at least in part by a porous membrane which surrounds and defines a reservoir. The reservoir contains a growth promoting hormone and a stabilizer. Examples of such stabilizers include certain polyols, amino acids, polymers of amino acids having a charged side group at physiological pH, and choline salts.

20 Claims, 1 Drawing Sheet

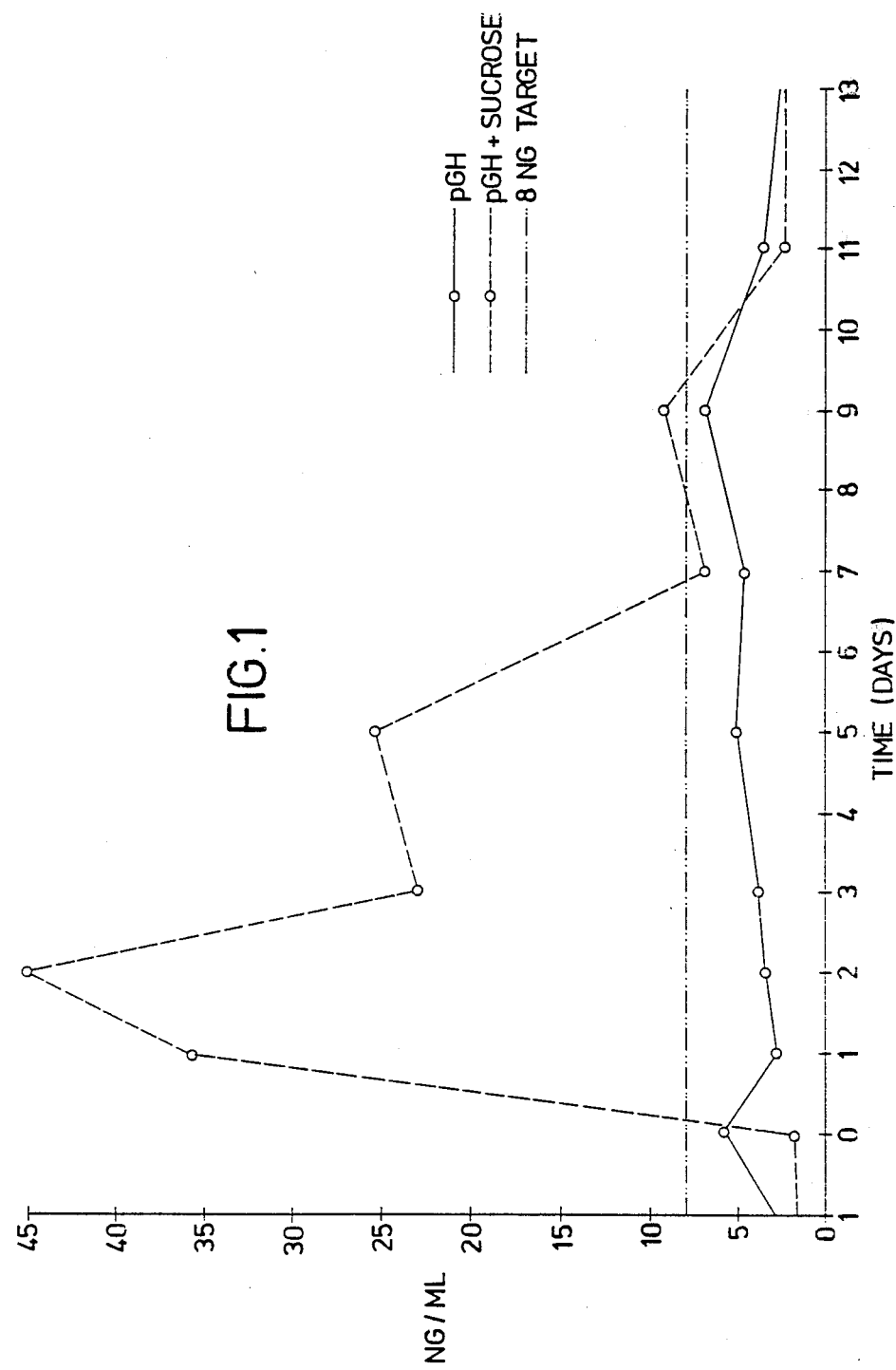

DELIVERY DEVICE FOR THE ADMINISTRATION OF STABILIZED GROWTH PROMOTING HORMONES

BACKGROUND OF THE INVENTION

The present invention relates to a delivery device for the administration for stabilized animal growth promoting hormone. The stabilizers decrease the formation of insolubles and preserve the soluble bioactivity of the growth promoting hormone in aqueous environments. One major problem in the administration of growth promoting hormones is the denaturation of the native globular structure causing aggregation of the growth hormone into precipitated forms which decreases the amount of active growth hormone available. The formation of these insolubles can also block tubing, membranes and various pumps of the implanted delivery devices. System failure almost always results due to the formation of these insolubles. In addition to the formation of insolubles, another problem in the administration of growth promoting hormones is retaining the soluble bioactivity of the hormone. Therefore, to properly serve as a stabilizer for growth promoting formulations, the stabilizer must decrease the formation of insolubles and maintain the bioactivity of the soluble growth hormone.

A variety of stabilizers have been disclosed in art which avoid the breakdown of the structures of proteins. For example, glycerol has been used to stabilize the activity of various proteins. Gekko, et al., *Biochemistry* (1981), 20, pp. 4666–76. Examples of proteins which are described in this article include chymotrypsinogen A (from bovine pancreas), ribonuclease A (from bovine pancreas), β-lactoglobin (from milk), bovine serum albumin, insulin (bovine pancreatic), egg-white lysozyme and α-chymotrypsin.

U.S. Pat. No. 4,179,337 discloses a process for coupling a polypeptide such as enzymes and insulin to polyethylene glycol or polypropylene glycol having a molecular weight of 500 to 20,000 daltons. The polyethylene glycol or polypropylene glycol is described as protecting the polypeptide from loss of activity and the composition can be injected without any immunogenic response.

U.S. Pat. No. 4,439,181 discloses a method for preventing the precipitation of proteins within drug delivery systems that depend on the fluidity of the infusate for proper function. The method comprises mixing a polyol with the protein solution prior to introduction of the solution into the drug delivery system. Examples of the polyols which are described include glycerol and biocompatible C-4 to C-18 polyols. Exemplary of the polyols are erythritol, arabinose, xylose, ribose, adonitol, arabitol, rhamose, inositol, fructose, galactose, glucose, mannose, sorbose, maltose, sucrose, melezitose, and raffinose. The solid polyols are dissolved in a standard aqueous insulin solution or are first prepared as an aqueous solution and admixed with the insulin to provide the final concentration of polyol in the solution of about 10 to 90 percent weight per volume, with the balance being the protein. Other proteins which are described as being subject to the same precipitation problems include growth hormone, glucagon and the like.

While the prior art has taught a number of various stabilizers for specific proteins, unfortunately, the fact a particular stabilizer is effective with a particular protein does not necessarily mean that the particular stabilizer is appropriate for the stabilization of a growth promoting hormone. Therefore, there exists a need for a method of stabilization of a growth promoting hormone which decreases the formation of insolubles and preserves the soluble bioactivity of the hormone.

SUMMARY OF THE INVENTION

The present invention concerns a delivery device designed to be implanted in an animal and for the administration of a stabilized growth promoting formulation. The device comprises a wall, formed at least in part by a porous membrane which surrounds and defines a reservoir containing a growth promoting hormone and a stabilizing amount of a stabilizer selected from one or more of the following:

(a) a polyol selected from the group consisting of non-reducing sugars, sugar alcohols, sugar acids, pentaerythritol, lactose, water-soluble dextrans and Ficoll;

(b) an amino acid selected from the group consisting of glycine, sarcosine, lysine or salts thereof, serin, arginine or salts thereof, betaine, N,N-dimethyl-glycine, aspartic acid or salts thereof, glutamic acid or salts thereof;

(c) a polymer of an amino acid having a charged side group at a physiological pH; and (d) a choline derivative selected from the group consisting of choline chloride, choline dihydrogen citrate, choline bitartrate, choline bicarbonate, tricholine citrate, choline ascorbate, choline borate, choline gluconate, choline phosphate, di(choline)sulfate and dicholine mucate.

BRIEF DESCRIPTION OF THE DRAWING

FIG. 1 is a graph showing the mean number of ng of porcine growth hormone per ml of blood serum corresponding to the time at which the blood serum sample was taken after implantation.

DETAILED DESCRIPTION OF THE PREFERRED EMBODIMENT

The present invention is directed to a delivery device for a stabilized animal growth promoting hormone. The stabilizers advantageously used in the present invention not only decrease the formation of insolubles but preserve the bioactivity of the soluble portion of the growth hormone. According to the present invention, an effective amount of a stabilizer is mixed with a growth promoting hormone prior to administration of the hormone to the animal. In one embodiment of the present invention, the stabilized growth promoting hormones are injected into the animal. In this embodiment, the stabilized growth hormones are in an aqueous solution comprising dissolved growth hormone and dissolved stabilizer. According to another embodiment of the present invention, the stabilized growth promoting hormones are administered via an implant device. According to this embodiment, the stabilized growth hormones can be in a liquid or dry state. Preferably, when an implant device is elected for the method of administration, the stabilized growth hormone is in the form of a dry mixture comprising solid growth hormone and solid stabilizer which, upon implantation in an aqueous environment, gets wetted and starts to dissolve.

The stabilizers are particularly suited for animal growth promoting hormones. Examples of such hormones include bovine, human, equine, avian, ovine and porcine growth promoting hormones. Preferably, the hormone is bovine or porcine growth promoting hormone. While the concentration of the growth promoting hormone may vary depending on the desired dosage and the particular growth promoting hormone, the hormone is generally present in amounts of from about 1 to about 97.5 percent by weight of the total weight of the growth promoting formulation. Preferably, the growth promoting hormone is present in amounts of from about 5 to about 50 percent of the overall weight of the growth promoting formulation. As one skilled in the art can appreciate, the growth hormones may comprise a high weight percent of the overall weight of the growth promoting formulation when the formulation is in the solid state since water and other suitable aqueous solvents are not needed to enable the formulation to be injectable.

The growth hormones for use in the present invention can be derived by extraction and subsequent concentration techniques from the pituitary glands of various animals. Growth hormones which are produced by recombinant DNA methods are also suitable. The amino acid sequences of various hormones which are suitable in the present invention are known. For example, the amino acid sequence of human growth promoting hormones is described in an article by C.H. Liu and Kirk-Othmer "Encyclopedia of Chemical Technology", 3rd E., Vol. 12, pp. 549–552. The amino acid sequence of bovine growth hormone is described in an article by R.P. Woychik, *Nucleic Acid Res.*, 10, 7197 (1982). The amino acid sequence of ovine growth hormone is described in an article by C.H. Liu et al., *Arch. Biochem. Biophys.*, 156, 493–508 (1973). The amino acid sequence of porcine growth hormone is described in an article by P.H. Seeburg et al., *DNA*, 2, 37, 45 (1983). All of the above references describing the amino acid sequences are hereby incorporated by reference in their entirety. In addition to the above, one can also use growth hormones that have been modified by excision of up to 12 amino acid residues from the amino ends of the amino acid sequences.

The stabilizers which are suitable for the present invention generally have two characteristics. First, they are generally very polar. Second, the stabilizers must be soluble in aqueous solutions. According to one embodiment, the stabilizer is preferably present in amounts sufficient such that when the stabilizer-growth formulation is in an aqueous environment or solution, the solution is saturated with the stabilizer. Obviously, the various stabilizers have their own respective solubilities and may be present in different amounts. When the growth promoting formulation is dispersed or dissolved in an aqueous solution, the stabilizer should be from about 5 percent by weight up to total saturation in the aqueous formulation containing the growth hormone. When the dry formulation is elected, the stabilizer may comprise higher weight percentages of the overall formulation since a major constituent, i.e. the water or aqueous solvent is eliminated. Accordingly, the respective weight percentages of the specific stabilizers listed below are inclusive of both aqueous formulations as well as solid formulations containing the stabilizer and growth promoting hormone.

Stabilizers which can be used in the present invention are polyols selected from non-reducing sugars, sugar alcohols, sugar acids, lactose, pentaerythritol, water soluble dextrans and Ficoll. One example of a non-reducing sugar is sucrose. Examples of sugar alcohols include mannitol, xylitol, erythritol, threitol, sorbitol and glycerol. An example of a sugar acid is L-gluconate and the metallic salts thereof. Preferably, the polyol is xylitol. Contrary to what one would believe after reading many of the prior art references and especially U.S. Pat. No. 4,439,181, not all polyols are appropriate for stabilizing growth promoting hormones. While many polyols may provide for the decrease in the formation of insolubles, some do not preserve the bioactivity of the soluble portion of the growth promoting hormone. Examples of such polyols include the reducing sugars for example, fructose, mannose, and maltose. Lactose, which is a reducing sugar, seems to be an exception to the remaining reducing skilled in the art will appreciate, the polyols which are used in the present invention have a variety of solubilities in water. While the amount of polyol is present in stabilizing amounts, the polyol can be present in amounts of from about 2.5 to about 99 percent by weight of the total weight of the overall formulation prior to introduction into an aqueous environment. Preferably, the polyol is present in amounts of from about 15 to about 80 percent by weight.

Other stabilizers which are suitable for the present invention are certain amino acids. Examples of amino acids which can be used include glycine, sarcosine, lysine or salts thereof, serine, arginine or salts thereof, betaine, N,N-dimethylglycine, aspartic acid or salts thereof, glutamic acid or salts thereof. Mixtures of such amino acids can also be used. Preferably, the amino acid is sarcosine. While the amino acid is present in stabilizing amounts, they are generally present in amounts of from about 2.5 to about 99 percent by weight of the total weight of the overall formulation prior to introduction into an aqueous environment. Preferably, the amino acid is present in amounts of from about 15 to about 80 percent by weight.

Certain polymers of amino acids have been found to be useful stabilizers for growth hormones. These polyamino acids or salts thereof can be characterized by charged side groups at physiological pH. The charge can be either "+" or "−". Some examples of polyamino acids which provide a stabilizing effect include polylysine, polyaspartic acid, polyglutamic acid, polyarginine, polyhistidine, polyornithine and salts of such polyamino acids. Preferably, the polyamino acid salt is poly DL-lysine HBr. Generally, these particular stabilizers are present in amounts of from about 2.5 to about 99 percent by weight of the total weight of the overall formulation. Preferably, the polyamino acid derivative is present in amounts of from about 15 to about 80 percent by weight.

Another class of stabilizers which can be used are derivatives of choline. Examples of such stabilizers include choline chloride, choline dihydrogen citrate, choline bitartrate, choline bicarbonate, tricholine citrate, choline ascorbate, choline borate, choline gluconate, choline phosphate, di(choline)sulfate and dicholine mucate. Preferably, the choline derivative is choline chloride. Generally, these stabilizers are present in amounts of from about 2.5 to about 99 percent by weight of the total weight of the overall formulation prior to introduction into an aqueous environment. Preferably, the choline derivative is present in amounts of from about 15 to about 80 percent by weight of the total weight of the overall formulation.

The preparation of the stabilized growth promoting formulations containing the stabilizer and the growth hormone may be by simple mechanical mixing. When an injectable form of the stabilized growth promoting formulation is desired, the stabilizer is first dispersed in an aqueous solution which can be stirred or shaken to bring about a more rapid solubilization of the stabilizer. After the aqueous solution of the stabilizer has been formed, the growth promoting hormone is added. The weight percentage of the aqueous solvent or water need only be an amount sufficient to dissolve the stabilizer and growth hormone and to allow the formulation to be administered by injection. Amounts ranging from about 40 to about 90 percent by weight are believed to be suitable. While the above procedure has been described as being the preferred, the order of addition can be altered and should be in no way deemed as limiting to the scope of the present invention. In another embodiment, the stabilizer and growth hormone can be wet or dry mixed to provide a solid formulation which is particularly suited for implants. After the growth hormone and the stabilizer have been mixed, any other optional additives, such as buffers, salts, adjuvants, etc., may be added.

Since the present growth hormone formulations are intended to be administered to an animal, the pH must be physiologically acceptable to the animal and not contribute to the destabilization of the growth promoting hormone. Generally, the pH of the stabilized growth promoting formulation ranges from about 4 to about 10, with the preferred pH range being from about 6.5 to about 8.0. The pH of the growth promoting formulation can be adjusted by effective amounts of a pharmaceutically acceptable base or acid to obtain the required pH. Suitable acids and bases are known to those skilled in the art.

The growth promoting formulations are for administration to an animal and preferably pigs and cows. These formulations can be administered in a variety of ways. I one embodiment, the growth promoting formulation can be in a liquid form or solution which is administered by subcutaneous injection or via a liquid containing reservoir of an implanted delivery device.

In another embodiment, the stabilized growth hormone formulation is compressed into tablet or pellet form prior to being placed in a reservoir of a delivery device. In order to formulate pellets from the stabilized growth promoting formulation, various binders are preferably used. Examples of binders which are suitable include sodium bentonite, ethyl cellulose, stearic acid, calcium stearate, adipic acid, fumaric acid, polyethylene glycol, deacetylated chitlon and cellulose acetate Generally, the binder is present in amounts of from about 0.5 to about 10 percent by weight of the total weight of the solid growth promoting formulation. Preferably, the binder is present in amounts of from 1 to about 5 percent by weight.

Lubricants are preferably added to the pellet to assist in the achievement of a sustained release pattern of the pellet and to assist in the ease of manufacture. Examples of such lubricants include those common tablet water insoluble lubricants such as, for example, magnesium stearate, sodium stearate, calcium stearate, powdered stearate acid, talc, paraffin, cocoa butter, graphite, lycopodium or combinations thereof. Preferably, the lubricant is a fatty acid derivative such as the stearates, including magnesium stearate, sodium stearate, and calcium stearate. While the amount of lubricant may vary, the lubricant is generally present in amounts of from about 0.5 to about 10 percent by weight of the total weight of the pellet. Preferably, the lubricant is present in amounts of from about 1 to about 5 percent by weight.

The stabilized growth hormone formulation, preferably pelletized, may be placed within the reservoir of a delivery device. The reservoir is defined and surrounded by a wall, at least a portion of which comprises a porous membrane. The materials suitable for forming the porous part of the external wall of the device are generally those through which the stabilizer and growth hormone can pass via pores. The pore size of the porous materials can be of from about 5 microns to about 250 microns with 10 to 100 microns being preferred. Suitable materials for forming these walls are naturally occurring or synthetic materials that are biologically compatible with body fluids, tissues and organs and essentially insoluble in body fluids with which the device will come into contact. The use of materials soluble in body fluids is undesirable, since dissolution of the wall of the device would affect both the rate of release of the growth hormone and the capability of the system to remain in place for prolonged periods of time. The material also desirably is characterized by constant porosity; if the porosity changes over time the rate of release of the growth hormone also will change over time.

Materials suitable for forming the porous portion of the wall of the device are known in the art as having a plurality of fused particles which provide a supporting structure having microscopic sized interconnecting pores. A variety of such materials are commercially available or can be made by different methods known in the art, including etched nuclear track, leaching, polyelectrolytic processes, ion exchange polymer reactions and other techniques. See, for example, *Synthetic Polymer Membranes*, R.E. Kesting, Chapters 4 and 5, published by McGraw-Hill, 1971; and *Chemical Reviews Ultrafiltration* 18: 363–455 (1934).

Microporous materials useful for making these parts of the devices of the present invention include microporous polyalkylenes, such as microporous polyethylene, microporous polycarbonates, microporous polyamides, microporous modacrylic copolymers, polyesters prepared by esterification of a dicarboxylic acid or anhydride with an alkylene polyol, phenolic polyesters, cross-linked olefin polymers, polyolefins, polyurethanes, polyimides, and polybenzimidazoles. Preferred microporous materials are microporous polyethylene.

As one skilled in the art can appreciate, the rate of diffusion of the contents of the reservoir will depend upon the particular material, the ingredients of the reservoir, pore size of the porous material and the dimensions of the porous materials, i.e., thickness and surface area. While the present invention is not limited to any particular dimensions of the porous portion of the device, excellent results have been achieved with microporous polyethylene discs having a pore size of from 10 to 70 microns, a diameter of 2 to 4 millimeters and thickness of 1.5 to 3 millimeters.

In the devices of this invention, typically only a portion of the external wall comprises a porous material. The remainder of the wall comprises a material that is essentially impermeable to the growth hormone and stabilizer(s) contained in the reservoir and to body fluids which are in contact with the implanted or inserted device. This portion of the external wall desirably is characterized much as the porous part of the wall was characterized above. The material should be compatible with body fluids, tissues and organs, and can comprise materials which are commercially available or can be made by processes known in the art. Suitable impermeable materials include steel or other suitable metals, acyl substituted cellulose acetates and alkyl derivatives thereof; partially and completely hydrolysed alkylene-vinyl acetate copolymers; unplasticized polyvinyl acetate, cross-linked homo- and copolymers of polyvinyl acetate; cross-linked polyesters of acrylic and methacrylic acid, polyvinyl alkyl ethers, polyvinyl fluoride, silicone, polycarbonate, polyurethane, polyamide, polysulphones, polyimides, polyolefins, polybenzimidazoles; styrene acrylonitrile copolymers, cross-linked poly(ethylene oxide), poly(alkylenes), poly(vinyl imidazole), poly(esters), chlorosulphonated polyolefins and ethylene-vinyl ester copolymers such as ethylene-vinyl acetate A preferred material is silicone.

The present invention is illustrated in further detail by way of the following examples which, however, are not to be construed as limiting the scope thereof.

EXAMPLE 1

Isotonic physiological phosphate buffer (IPPB) having a pH of 7.3 was prepared from sodium hydrogen phosphates (0.1 F phosphates) plus 0.2% $NaN_3$. Using this buffer, solutions of additives were prepared as shown in Table 1. Then ca. 40 mg portions of bovine growth hormone in 50 ml sterile centrifuge tubes were wetted with 100 μl of the solutions. The tubes were stored at 37° C. Following the time at 37° C. (see Table 1 for times) each 50 ml tube was typically handled as follows. First, 40 ml of IPPB was added to the tube (defined as start of solubilization time). Using a cup sonicator, the wetted material in the tube was effectively suspended/dissolved. The resulting suspension was subsequently vortexed during a period of standing at room temperature. The respective tube was centrifuged for ca. 5 min. ×1900 G (defined as the end of solubilization time). The resulting supernatant was nearly all removed by pipet and the undissolved residue suspended in 20 ml added water. Following centrifugation and supernatant removal, the residue in the tube was dried at room temperature in a Savant Speed Vac Concentrator to a final chamber pressure of ca. 150 mT. The pelleted dry residue was removed from the tube and its weight determined by the difference weight of the tube.

In the tables below, radio receptor assays (RRA) and hypox growth test results are given on several of the formulations. The entry "+" indicates substantially 100% activity relative to native bovine growth (bGH) standard, "−" indicates little or no activity and "<" indicates some intermediate level of activity. Two symbols designate an "in-between" result.

In the following examples, the bovine growth hormones identified as Lot 7500(1), Lot 7237C, Lot 8096C and 7500 were Parlow purified pituitary growth hormones which were purchased from A.F. Parlow of the University of California School of Medicine, Harbor General Hospital, Torrance, Calif.

TABLE 1

| Formulation | bGH Used | Additive | Weight % of Additive in Solution | Days @ 37° C. | Solub. Time (h) | Insolubles As Wt. % of Starting bGH | RRA | Hypox Rat Growth |
|---|---|---|---|---|---|---|---|---|
| 1 | Lot 7500(1) | Sucrose | 5 | 22 | 1.6 | 39 | + | |
| 2 | Lot 7500(1) | Sucrose | 16 | 21 | 1.5 | 20 | | |
| 3 | Lot 7500(1) | Sucrose | 50 | 20 | 1.3 | 6 | | |
| 4 | Lot 7237C | Sucrose | 50 | 15 | 2.5 | 5 | + | + |
| 5 | Lot 7237C | Mannitol | 15 | 19 | 1.7 | 20 | +(<) | |
| 6 | Lot 7500(1) | Mannitol | 15 | 20 | 2.3 | 21 | | |
| 7 | Lot 7500(1) | Sorbitol | 50 | 20 | 1.3 | 6 | + | |
| 8 | Lot 7237C | Sorbitol | 50 | 19 | 1.7 | 9 | + | + |
| 9 | Lot 7237C | Sorbitol | 41 | 20 | 1.5 | 5 | <(+) | |
| 10 | Lot 7237C | Lactose | 15 | 19 | 1.5 | 12 | + | + |
| 11 | Lot 7237C | Lactose | 52 | 20 | 1.5 | 5 | +(<) | |
| 12 | Lot 7500(1) | Ficoll | 24 | 21 | 1.5 | 26 | | |
| 13 | Lot 7237C | Ficoll | 19 | 19 | 2.6 | 23 | + | |
| 14 | Lot 7500(1) | Glycerol | 51 | 19 | 0.75 | 17 | + | |
| 15 | Lot 7237C | Glycerol | 51 | 19 | 1.5 | 10 | + | + |
| 16 | Lot 7500(1) | Glycine | 5 | 22 | 1.6 | 35 | | |
| 17 | Lot 7500(1) | Glycine | 15 | 22 | 3.0 | 19 | | |
| 18 | Lot 7500 | Glycine | 15 | 17 | 2.3 | 13 | | |
| 19 | Lot 7500(1) | Glycine | 15 | 17 | 2.3 | 14 | | |
| 20 | Lot 7237C | Glycine | 15 | 19 | 1.5 | 16 | + | + |
| 21 | Lot 7237C | Glycine | 15 | 20 | 1.5 | 16 | | |
| 22 | Lot 7237C | Sarcosine | 5 | 20 | 1.7 | 46 | | |
| 23 | Lot 7237C | Sarcosine | 15 | 20 | 1.7 | 31 | | |
| 24 | Lot 7237C | Sarcosine | 30 | 20 | 1.7 | 8 | | + |
| 25 | Lot 7237C | Sarcocine | 30 | 20 | 1.7 | 12 | | |
| 26 | Lot 7237C | Sarcosine | 40 | 20 | 1.7 | 11 | | |
| 27 | Lot 7237C | Poly DL-lysine HBR (MW = 37 K) | 29 | 19 | 1.5 | 16 | | |
| 28 | Lot 7237C | Betaine | 45 | 20 | 1.7 | 20 | + | |
| 29 | Lot 7237C | Poly-L-aspartate Na+ (14000) | 28 | 19 | 1.5 | 12 | + | |
| 30 | Lot 7237C | Choline Chloride | 50 | 21 | 1.5 | 10 | + | |
| 31 | Lot 7237C | L-arginine HCl | 45 | 20 | 1.5 | 8 | + | |
| 32 | Lot 7237C | Na+ D-gluconate- | 33 | 20 | 1.5 | 7 | + | |
| 33 | Lot 8096C | Na+ L-aspartate- | 46 | 19 | 1.5 | 14 | + | |
| 34 | Lot 8096C | L-arginine | 39 | 20 | 1.5 | 13 | + | |

TABLE 1-continued

| Formulation | bGH Used | Additive | Weight % of Additive in Solution | Days @ 37° C. | Solub. Time (h) | Insolubles As Wt. % of Starting bGH | RRA | Hypox Rat Growth |
|---|---|---|---|---|---|---|---|---|
| 35 | Lot 8096C | L-aspartate L-lysine | 50 | 19 | 1.5 | 11 | + | |
| 36 | Lot 7237C | L-aspartate N,N-dimethylglycine | 30 | 20 | 1.7 | 27 | + | |
| | | NaCl | 17 | | | | | |
| 37 | Lot 7237C | Poly-L-glucate Na+ (60000) | 17 | 19 | 2.0 | 18 | + | |
| 38 | Lot 7237C | Poly-L-ornithine | 30 | 19 | 1.5 | 18 | + | |
| 39 | Lot 7237C | Poly-L-glutamate-Na+ (60000) | 17 | 19 | 2.0 | 18 | + | |

EXAMPLE 2

CONTROL EXPERIMENTS

A number of control experiments were conducted following the procedure of Example 1. Table 2 below lists the respective data from these control experiments. As can be seen from Table 2 below, IPPB solution alone provides from about 39 to about 52 weight percent of insolubles. Therefore, any decrease in the amount of insolubles below this range is viewed as an improvement. Many of the candidates in the table below, while providing a substantial decrease in the formation of insolubles, do not retain the bioactivity to an acceptable level. Surprisingly, many of the polyols which are described in the prior art as being suitable stabilizers for maintaining the fluidity of various proteins are not suitable for use with growth promoting hormones.

conducted as follows. Into a 50 ml tube was charged dry additive plus dry growth hormone and IPPB. THe tubes were then sealed and incubated at 37° C. for 19 days. After incubation, the samples were analyzed in the same manner as in the Example 1. Table 3 lists the data from the dry additive experiments. The data in Table 3 indicates that the reductions in insolubles were not clearly different than in Example 1 where the additive was first dissolved in solution. Thus, the simulated implant experiments demonstrate the effectiveness of the present invention.

TABLE 3

DRY FORMULATIONS

| Formulation | bGH Used | Additive | Wt of bGH | Wt of Additive in Solution | Amount of IPPB (ul) | Days @ 37° C. | Insolubles As Wt. % of Starting bGH | RRA | Hypox Rat Growth |
|---|---|---|---|---|---|---|---|---|---|
| 1 | Lot 7237C | Pentaerythritol | 40 mg | 47 mg | 100 | 19 | 27 | + | |
| 2 | Lot 7237C | L-Serine | 40 mg | 41 mg | 150 | 19 | 19 | + | |

EXAMPLE 4

To demonstrate the effectiveness of an implant device containing porcine growth hormone and a stabilizer compared to an implant device containing only porcine growth hormone, the following experiments were conducted. Into each of 20 hollow silicon tubes measuring

TABLE 2

CONTROLS

| Formulation | bGH Used | Additive | Weight % of Additive in Solution | Days @ 37° C. | Solub. Time (h) | Insolubles As Wt. % of Starting bGH | RRA | Hypox Rat Growth |
|---|---|---|---|---|---|---|---|---|
| 1 | Lot 7500(1) | IPPB | — | 15 | 28 | 52 | | |
| 2 | Lot 7237C(1) | IPPB | — | 19 | 2.3 | 39 | + | |
| 3 | Lot 7500(1) | Dextrose | 15 | 23 | 3.2 | 14 | < | < |
| 4 | Lot 7237C | Dextrose | 51 | 15 | 2.3 | 2 | −(<) | < |
| 5 | Lot 7237C | Mannose | 51 | 19 | 1.7 | 3 | — | + |
| 6 | Lot 7237C | Fructose | 50 | 19 | 1.7 | 10 | — | |
| 7 | Lot 7237C | Maltose | 28 | 19 | 2.6 | 10 | < | |
| 8 | Lot 7237C | Polyethylene Glycol (MW = 400) | 20 | 18 | 2.5 | 36 | + | + |
| 9 | Lot 7500(1) | Ethylene Glycol | 50 | 21 | 1.5 | 83 | | |
| 10 | Lot 7237C | Ethylene Glycol | 50 | 19 | 2.6 | 80 | | |

EXAMPLE 3

Two experiments were conducted using Parlow bGH which was dry mixed with a stabilizer to simulate the conditions of an implant. The wetting experiments were 2 cm ×0.7 cm. was inserted a teflon circular disc in order that each tube has two equal size compartments. In each compartment of 10 tubes (hereinafter Tubes A) was inserted 20 mg of Parlow (Lot 4556) porcine growth hormone. The tubes were then sealed on each end with a microporous polyethylene disc having a pore size of 70 microns. The remaining 10 tubes (hereinafter Tubes B) were prepared in the same manner except that the Parlow porcine growth hormone was a mixture of lots 4654 and 4673. No significant difference between the growth hormone used in tubes A and tubes B was detected. In addition to the growth hormone, tubes B additionally contained 80 mg of sucrose which was homogeneously mixed with the growth hormone prior to insertion into the tubes.

Each tube was implanted subcutaneously behind ear of a pig. Thereafter, the presence of growth hormone in each pig was measured by analysis of the blood serum levels. The growth hormone was measured in units of ng/ml.

Table 4 below lists the mean number of ng of porcine growth hormone per ml of blood serum corresponding to the time at which the blood serum sample was taken after implantation.

FIG. 1 plots out the data of table 2. In addition, a line is drawn to depict a minimal desired level of 8 ng/ml of growth hormone.

These experiments demonstrate that the stabilized growth hormone formulations provide for higher concentrations of growth hormone in the serum than growth hormone alone.

TABLE 4

EFFECT OF DELIVERY SYSTEMS ON LEVELS OF GROWTH HORMONE IN BLOOD SERUM

| Day | Delivery System | |
| --- | --- | --- |
|  | A | B |
| 1 | 2.8 | 35.8 |
| 2 | 3.4 | 45.0 |
| 3 | 3.8 | 23.2 |
| 5 | 5.1 | 25.4 |
| 7 | 4.6 | 7.0 |
| 9 | 6.9 | 9.3 |
| 11 | 4.4 | 2.4 |
| 13 | 2.7 | 2.0 |

The above means were adjusted by covariance with the mean blood growth hormone level on the day prior to implantation and for day 0.

What is claimed is:

1. A delivery device designed to be implanted in an animal and for the administration of a stabilized growth promoting formulation, said device comprising a wall, formed at least in part by a porous membrane, which surrounds and defines a reservoir containing a growth hormone and a stabilizing amount of a stabilizer which inhibits aggregation and bioinactivation of the growth hormone selected from one or more of the following:
   (a) a polyol selected from the group consisting of non-reducing sugars, sugar alcohols, sugar acids, lactose, pentaerythritol, water-soluble dextrans, and Ficoll;
   (b) an amino acid selected from the group consisting of glycine, sarcosine, lysine or salts thereof, serine, arginine or salts thereof, betaine, N,N-dimethylglycine, aspartic acid or salts thereof, glutamic acid or salts thereof; and
   (c) a choline derivative selected from the group consisting of choline chloride, choline dihydrogen citrate, choline bitartrate, choline bicarbonate, tricholine citrate, choline ascorbate, choline borate, choline gluconate, choline phosphate, di(choline) sulfate and dicholine mucate.

2. The delivery device of claim 1, wherein said formulation is in the form of a pellet.

3. The delivery device of claim 2, wherein said formulation additionally comprises a binder and a lubricant.

4. The delivery device of claim 3, wherein said binder is selected from the group consisting of sodium bentonite, ethyl cellulose, stearic acid, calcium stearate, adipic acid, fumaric acid, polyethylene glycol, deacetylated chitlon and cellulose acetate; and said lubricant is selected from the group consisting of magnesium stearate, sodium stearate, calcium stearate, powdered stearate acid, talc, paraffin, cocoa butter, graphite, lycopodium or combinations thereof.

5. The delivery device of claim 1 wherein said growth hormone is selected from the group consisting of ovine, porcine, equine, avian, human and bovine growth hormones.

6. The delivery device of claim 5 wherein said growth hormone is bovine growth promoting hormone.

7. The delivery device of claim 1 wherein said growth hormone is present in amounts of from 1 to about 97.5 percent by weight and said stabilizer is present in amounts of from 97.5 to 1 percent by weight.

8. The delivery device of claim 4 wherein said binder is present in amounts of from about 0.5 to about 10 percent by weight of the total weight of pellet.

9. The delivery device of claim 8 wherein said lubricant is present in amounts of from 5 to about 10 percent by weight of the total weight of the pellet.

10. A stabilized growth promoting formulation, comprising:
    a growth hormone, and
    a stabilizing amount of a stabilizer which inhibits aggregation and bioinactivation of the growth hormone selected from one or more of the following:
    (a) a polyol selected from the group consisting of non-reducing sugars, sugar alcohols, sugar acids, lactose, pentaerythritol, water-soluble dextrans, and Ficoll;
    (b) an amino acid selected from the group consisting of glycine, sarcosine, lysine or salts thereof, serine, arginine or salts thereof, betaine, N,N-dimethylglycine, aspartic acid or salts thereof, glutamic acid or salts thereof; and
    (c) a choline derivative selected from the group consisting of choline chloride, choline dihydrogen citrate, choline bitartrate, choline bicarbonate, tricholine citrate, choline ascorbate, choline borate, choline gluconate, choline phosphate, di(choline) sulfate and dicholine mucate.

11. The growth promoting formulation of claim 10, wherein said formulation is an aqueous solution comprising dissolved growth hormone and dissolved stabilizer.

12. The growth promoting formulation of claim 10, wherein said formulation is in the form of a dry mixture comprising solid growth hormone and solid stabilizer.

13. The growth promoting formulation of claim 12, wherein said formulation is in the form of a pellet.

14. The growth promoting formulation of claim 13, wherein said formulation additionally comprises a binder and a lubricant.

15. The growth promoting formulation of claim 14, wherein said binder is selected from the group consisting of sodium bentonite, ethyl cellulose, stearic acid, calcium stearate, adipic acid, fumaric acid, polyethylene glycol, deacetylated chitlon and cellulose acetate; and said lubricant is selected from the group consisting of magnesium stearate, sodium stearate, calcium stearate, powdered stearate acid, talc, paraffin, cocoa butter, graphite, lycopodium or combinations thereof.

16. The growth promoting formulation of claim 14 wherein said binder is present in amounts of from about 0.5 to about 10 percent by weight of the total weight of pellet.

17. The growth promoting formulation of claim 14 wherein said lubricant is present in amounts of from 5 to about 10 percent by weight of the total weight of the pellet.

18. The growth promoting formulation of claim 10 wherein said growth hormone is selected from the group consisting of ovine, porcine, equine, avian, human and bovine growth promoting hormones.

19. The growth promoting formulation of claim 18 wherein said growth hormone is bovine growth promoting hormone.

20. The growth promoting formulation of claim 10 wherein said growth promoting hormone is present in amounts of from 1 to about 97.5 percent by weight and said stabilizer is present in amounts of from 97.5 to 1 percent by weight.

* * * * *

UNITED STATES PATENT AND TRADEMARK OFFICE
CERTIFICATE OF CORRECTION

PATENT NO. : 4,917,685
DATED : April 17, 1990
INVENTOR(S) : Ravi Viswanathan and Randolph B. DePrince It is certified that error appears in the above-identified patent and that said Letters Patent is hereby corrected as shown below:

Column 1, line 28, before "art", insert --the--

Column 5, line 37, "I" should read --In--

Column 7, line 16, following "acetate", insert --.--

Column 12, Claim 20, line 2, delete the word --promoting--

Column 11, Claim 1, line 61, following "salts thereof;" start a new line and insert --(c) a polymer of an amino acid having a charged side group at physiological pH; and--

Column 11, Claim 1, line 62, delete the word --and--

Column 11, Claim 1, line 63, "(c)" should read --(d)--

Column 12, Claim 10, line 45, following the word "and", start a new line and insert --(c) a polymer of an amino acid having a charged side group at physiological pH; and--

Column 12, Claim 10, line 45, delete the word --and--

Column 12, Claim 10, line 46, "(c)" should read --(d)--

Signed and Sealed this

Twelfth Day of November, 1991

Attest:

HARRY F. MANBECK, JR.

*Attesting Officer*        *Commissioner of Patents and Trademarks*